(12) United States Patent
Forsythe et al.

(10) Patent No.: US 8,685,339 B2
(45) Date of Patent: Apr. 1, 2014

(54) FIELD AND STORAGE CHEMICAL TEST KIT

(75) Inventors: John M. Forsythe, Nampa, ID (US); Jan W. de Weerd, Meridian, ID (US)

(73) Assignee: PIN/NIP, Inc., Meridian, ID (US)

( * ) Notice: Subject to any disclaimer, the term of this patent is extended or adjusted under 35 U.S.C. 154(b) by 1317 days.

(21) Appl. No.: 10/719,718

(22) Filed: Nov. 21, 2003

(65) Prior Publication Data
US 2013/0071301 A1    Mar. 21, 2013

(51) Int. Cl.
*G01N 1/34* (2006.01)
*G01N 1/00* (2006.01)

(52) U.S. Cl.
USPC ............................................. 422/430; 422/50

(58) Field of Classification Search
USPC .................. 422/61, 50, 430; 436/20
See application file for complete search history.

(56) References Cited

U.S. PATENT DOCUMENTS

| | | | |
|---|---|---|---|
| 420,780 A * | 2/1890 | Fraue ........................... | 30/279.6 |
| 1,218,566 A * | 3/1917 | Kawakubo ...................... | 30/299 |
| 3,445,246 A * | 5/1969 | Martin ........................... | 426/312 |
| 3,506,458 A * | 4/1970 | Martin ........................... | 426/320 |
| 3,675,490 A | 7/1972 | Blomquist | |
| 4,123,558 A * | 10/1978 | Poapst et al. ................... | 426/268 |
| 4,492,759 A | 1/1985 | Gorman et al. | |
| 4,596,073 A * | 6/1986 | Ewald .......................... | 30/113.1 |
| 4,613,575 A | 9/1986 | Westrup et al. | |
| 4,686,192 A * | 8/1987 | Fisher ........................... | 436/60 |
| 4,714,614 A | 12/1987 | Scher | |
| 4,812,413 A | 3/1989 | Glattstein et al. | |
| 4,873,193 A * | 10/1989 | Jensen et al. ................... | 436/176 |
| 4,900,663 A | 2/1990 | Wie et al. | |
| 4,992,379 A | 2/1991 | Hanby | |
| 5,028,543 A | 7/1991 | Finch et al. | |
| 5,081,010 A | 1/1992 | Cummins et al. | |
| 5,244,866 A * | 9/1993 | Tayler .......................... | 504/253 |
| 5,358,851 A | 10/1994 | Peck | |
| 5,436,226 A * | 7/1995 | Lulai et al. ..................... | 504/291 |
| 5,520,041 A * | 5/1996 | Haswell ........................ | 73/29.04 |
| 5,622,912 A * | 4/1997 | Riggle et al. ................... | 504/143 |
| 5,623,084 A * | 4/1997 | Ruminski ....................... | 558/54 |
| 5,635,452 A * | 6/1997 | Lulai et al. ..................... | 504/324 |
| 5,728,350 A | 3/1998 | Kinoshita et al. | |
| 5,843,311 A * | 12/1998 | Richter et al. ................. | 210/634 |
| 5,907,925 A | 6/1999 | Guyot | |
| 5,958,714 A | 9/1999 | Gordon et al. | |
| 5,965,489 A | 10/1999 | Forsythe et al. | |
| 6,312,754 B1 * | 11/2001 | Wong ........................... | 426/633 |
| 6,324,927 B1 | 12/2001 | Ornath et al. | |
| 6,580,067 B1 | 6/2003 | Yamada et al. | |
| 6,610,908 B1 | 8/2003 | Chapple | |
| 2001/0053517 A1 * | 12/2001 | Anton et al. .................... | 435/6 |
| 2002/0085953 A1 | 7/2002 | Parker | |
| 2002/0132271 A1 | 9/2002 | Onisk et al. | |
| 2002/0150504 A1 | 10/2002 | Nunes et al. | |
| 2005/0059162 A1 | 3/2005 | Wohleb | |

FOREIGN PATENT DOCUMENTS

| | | |
|---|---|---|
| EP | 0 832 689 A2 | 4/1998 |
| WO | 01/92879 A1 | 12/2001 |

OTHER PUBLICATIONS

Atlantic Publishing Company Garnishing Tools online advertisement.*
Beveridge et al, J. L., Dalziel, J.; Duncan, H. "The assessment of some volatile organic compounds as sprout suppressants for ware and see potatoes." J. Potato Research. 1981, 24, 64-76.*
Bushway, R. J.; Bureau, J. L.; King, J. "Modification of the Rapid High Performance Liquid Chromatographic Method for the Determination of Potato Glocoalkaloids." J. Agric. Food Chem. 1986, 34, 277-279.*
Friedman, M.; McDonald, G. M. "Acid-Catalyzed Parital Hydrolysis of Carbohydrate Groups of the Potato Glycoalkaloid a-Chaconine in Alocoholic Solutions." J. Agric. Food Chem. 1995, 43, 1501-1506.*
Friedman, M.; McDonald, G.; Haddon, W. F. "Kinetics of Acid Catalyzed Hydrolysis of Carbohydrate Groups of Potato Glycoalkaloids a-Chaconine and a-Solanine." J. Agric. Food Chem. 1993, 41, 1397-1406.*
Yada, R.Y.; Coffin, R.H.; Keenan, M.K.; Fitts, M.; Dufault, C.; Tai, G.C.C."The Effect of Maliec Hydrazinde (Potassium salt) on Potato Yield, Sugar Content, and Chip Color of Kennebec and Norchip Cultivars." Am. Potato J. 1991, 68, 705-709.*
Environmental Protection Agency. 40 CFR PArt 180, [OPP-2003-0127; FRL-7321-6]. "2,6-diisopropylnaphthalene: Temporary Tolerances." Federal Register. vol. 68, No. 153, Aug. 8, 2003, pp. 47246-47253.*

(Continued)

*Primary Examiner* — Christine T Mui
(74) *Attorney, Agent, or Firm* — TraskBritt

(57) ABSTRACT

Methods and kits for assaying a chemical in a sample are disclosed. The method includes placing an extraction solution and an internal standard in a container. A sample is collected from a first location and placed in the container. The container is transported to a second location where the chemical in the extraction solution is assayed. A kit for transporting the sample from a first location to a second location includes at least one container for holding the sample. The at least one container includes an extraction solution for dissolving a chemical in the solution and an internal standard for calibrating an assay of the chemical. The methods and kits may be used in a system for quantitating an amount of a sprout inhibitor on a tuber, such as a potato.

2 Claims, 1 Drawing Sheet

(56) References Cited

OTHER PUBLICATIONS

Shelton, L. R.; Capel, P. D. "Guidelines for Collection and Processing Samples of Stream Bed Sediments for Analysis of Trace Elements and Organic Contanimants for the National Water-Quality Assessment Program." U.S. Geological Survey. Open-File Report 94-458, 1994.*

Wilde, F.D.; Radtke, D. B.; Gibs, J.; Iwatsubo, R.T. "Chapter A5 Processing of Water Samples." National Field Manual for the Collection of Water-Quality Data. Book 9 Handbooks for Water Resources Investigations, U.S. Geological Survey TWRI Book 9, (Version 2) Date: Apr. 4, 2002.*

Untied States Environmental Protection Agency, EPA 542-F-01-009. "A Citizen's Guide to Solvent Extraction." Publication Date: Oct. 2001. 2 pages.*

Prest, H. Solid-phase Extraction and Retention-Time Locked GC/MS Analysis of Selected Polycyclic Aromatic Hydrocarbons (PAHs). Agilent Technologies, Inc. Date: Jul. 12, 2002. pp. 1-14.*

Office Action mailed on Aug. 13, 2009 for U.S. Appl. No. 10/719,929. 7 pages.*

The 1998 Aldrich Catalog, three pages.*

Agilent Technologies Life Sciences/Chemical Analysis Online Store web archive date: Sep. 18, 2002, three pages.*

Scrivens, W. A.; Tour, J. M. "Potent Solvents for C60 and Their Utility for the Rapid Acquisition of 13C NMR Data for Fullerenes," J. Chem. Soc. Chem. Commun., 1993, pp. 1207-1209.*

Biedermann et al., "Two GC-MS Methods for the Analysis of Acrylamide in foods," Mitt. Lebensm. Hyg. 93, 638-652 (2002).

Walz, Rainer, "Determination of Acrylamide in food," Analytix, vol. 4, Sep. 1, 2003, pp. 1-18.

European Search Report for EP 10172206, dated Nov. 10, 2010, 9 pages.

Fetzer, "The chemistry and analysis of large PAHs," Polycyclic Aromatic Compounds, 2007, pp. 143-162, vol. 27.

Written Opinion for PCT/US2004/038829, dated Apr. 7, 2005.

International Preliminary Report on Patentability for PCT/US2004/038829, dated Dec. 12, 2005.

Edwards, Everhard J., et al., "Improved High-Performance Liquid Chromatographic Method for the Analysis of Potato (*Solanum tuberosum*) Glycoalkaloids," J. Agric. Food Chem., vol. 44, No. 9, 1996, pp. 2705-2709.

Escuderos-Morenas, M.L., et al., "Direct determination of monolinuron, linuron and chlorbromuron residues in potato samples by gas chromatography with nitrogen-phosphorus detection," J. Chromatogr. A. 1011, 2003, pp. 143-153.

PCT International Search Report, dated Apr. 7, 2005.

* cited by examiner

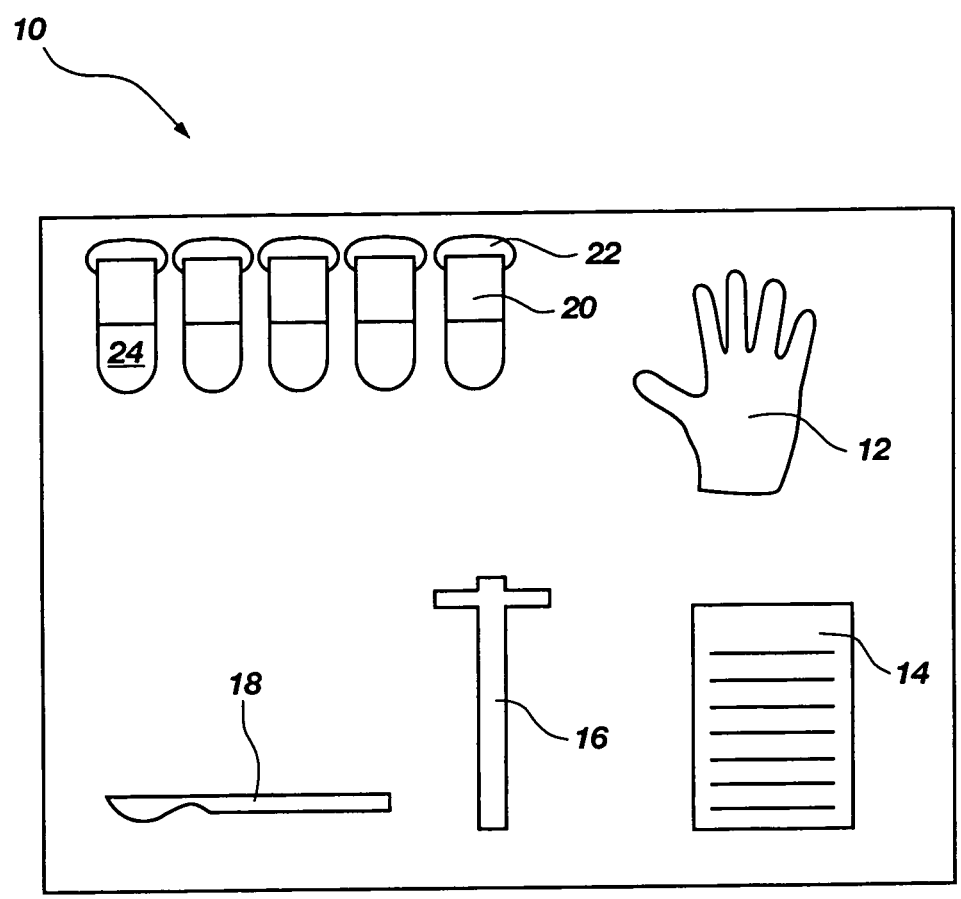

FIELD AND STORAGE CHEMICAL TEST KIT

TECHNICAL FIELD

The present invention relates generally to methods and kits used to test for the presence of chemical residues, and more specifically, to methods and kits for assaying chemical residues on a crop.

BACKGROUND

Chemicals are present in virtually all aspects of the environment in which humans live. For instance, herbicides and pesticides are used in agriculture to more efficiently and economically produce food. Likewise, industrial chemicals are used in many aspects of the manufacturing industry to fabricate and produce the goods that we use. The widespread use of these various chemicals requires methods of detection in order to most efficiently use the various chemicals.

Methods of detecting chemicals are used in disciplines other than agriculture and industry. For instance, contaminants in soil and water are monitored to keep in line with environmental regulations. Also, prohibited substances, such as illegal drugs, chemical weapons, biological weapons and explosives, may be screened for in various contexts. The various chemicals may be screened for at the site, or in the field, where the sampling occurs or samples may be taken at the site and transported to a laboratory for analysis or testing.

U.S. Pat. No. 4,492,759 to Gorman et al. discloses a qualitative test for detecting asbestos. The qualitative test is performed with a field test kit that includes the reagents and tubes required to perform the test. A sample is placed in a column of the test kit and various reagents are added to, and removed from, the sample in the column. If the tested sample contains asbestos, a color develops and indicates the presence of the asbestos. Another field test kit is disclosed in U.S. Pat. No. 4,992,379 to Hanby. The field test kit in Hanby is used to qualitatively and quantitatively test for aromatics in soil and groundwater. The field test kit includes items for performing the test, wherein a characteristic color is developed if the contaminating aromatics are present in a sample.

Presently, tissue samples are collected from the potatoes at a first location, such as a potato storage facility, where the potatoes have been treated with the sprout inhibitor or sprout suppressant for storage. The potatoes are collected from a potato storage facility and transported to a second location, such as a laboratory, where the presence of the sprout inhibitor an/or sprout suppressant, such as DMN and/or CIPC, is quantitatively measured or otherwise analyzed. Conventional methods of analyzing the amount of CIPC on the potatoes include sending whole potatoes in a bag from the potato storage facility to the laboratory. DMN is typically transported in a sealed container, such as a one gallon metal can, from the potato storage facility to the laboratory.

Although some field test kits include components that allow testing to be performed on site in the field, other tests require conditions or equipment that are not practical or economical for performance in the field. For example, the testing may require the use of a detection apparatus that is too expensive or too large to be efficiently transported to, and used in, the field. In such cases, the tests are performed in a laboratory.

There are a number of disadvantages associated with transporting the sample to the laboratory. These include the expense associated with transporting the sample to the laboratory or testing facility, loss of sample integrity during transport (i.e., some chemicals are volatile), and damage to the contents of the sample during transport. Thus, a need exists for more efficient methods for collecting a sample thought to include a chemical residue and transporting the sample thought to contain the chemical residue to a laboratory for testing. Such methods should preserve the integrity of the sample and provide efficient transport of the sample to the laboratory.

SUMMARY OF THE INVENTION

In one exemplary embodiment, a method for assaying a chemical is disclosed. The method includes depositing an extraction solution and a predetermined amount of an internal standard in a container. A sample is collected from a first location and placed in the container such that the sample contacts the extraction solution. The container including the sample is transported from the first location to a second location where the chemical in the extraction solution is quantitatively measured. The method may be used to assay any chemical, including, for example, a pesticide, a sprout inhibitor, a disinfectant, or a sprout suppressant.

In another exemplary embodiment, a kit for transporting a sample from a first location to a second location is described. The kit comprises at least one container for holding the sample. The at least one container includes an extraction solution for dissolving a chemical in the sample and an internal standard for calibrating a quantitative measurement of the chemical.

In a further exemplary embodiment, a method for analyzing a sprout inhibitor or sprout suppressant on a tuber is disclosed. The method includes collecting a sample from the tuber at a first location and depositing the sample into a container that includes an extraction solution. The container including the sample is transported to a second location where the sprout inhibitor in the extraction solution is assayed.

A kit for transporting a tuber sample from a first location to a second location is described in another exemplary embodiment. The kit comprises at least one container for holding the tuber sample, an extraction solution for dissolving a sprout inhibitor on the tuber sample and, optionally, an internal standard for calibrating an assay of the sprout inhibitor of the tuber sample.

In another exemplary embodiment, a system for quantitatively measuring an amount of a chemical on a tuber is disclosed. The system includes a sampling means for collecting a sample from the tuber. The system further includes a kit comprising at least one container for holding the sample, an extraction solution for dissolving the chemical on the tuber sample and an internal standard for calibrating the assaying of the chemical on the tuber. A means for quantitatively measuring an amount of the chemical in the extraction solution is also within the system.

BRIEF DESCRIPTION OF THE DRAWINGS

The nature of the present invention, as well as other embodiments of the present invention, may be more clearly understood by reference to the following detailed description of the invention, to the appended claims, and to the drawings herein, wherein FIG. 1 is a diagram illustrating components of a kit of the present invention.

DETAILED DESCRIPTION

The instant invention relates to methods, kits and a system for collecting and transporting samples thought to include a chemical residue from a first location to a second location. In the exemplary embodiments, one or more samples are collected and placed into a sealable container that includes an extraction solution. The sealable containers including the samples are transported to a second location, such as a laboratory, for subsequent analysis or quantitative measurement. However, the invention is not meant to be so limited. The methods, kits and system described herein also have utility in collecting samples from all types of crops, soil, water, food, various points in industrial processes, or from any other location or source at the first location, wherein the samples are transported to the second location for testing.

In one exemplary embodiment, a method for analyzing an amount of chemical on a crop is disclosed. In the exemplary embodiment, the crop is a tuber, such as a potato, and the chemical is a sprout inhibitor, such as 1,4-dimethylnaptha-lene (1,4 DMN). It will be apparent to those of ordinary skill in the art that the methods, kits and system described herein may be used to analyze any type of chemical on any type of crop, including other vegetables, fruits, grains, tubers or other types of samples (e.g., soil, water, food). Other chemicals that may be analyzed include, without limitation, herbicides, pesticides, fertilizers, hydrocarbons, aromatics, growth hormones (e.g., gibrellic acid, naphthyl acetic acid, etc.) and other known chemicals. In addition to DMN, other sprout inhibitors (sprout suppressants) that may be analyzed include, but are not limited to, chlorpropham (CIPC), diisopropylnaphthalene, aromatic acids, maleic hydrazide, hydrogen peroxide plus (HPP), jasmonates, acetohydroxyacid synthase (AHAs), carvone, any combination of these chemicals, and any other type of sprout inhibitor known by those of ordinary skill in the art.

In the exemplary embodiment, the tissue samples are collected from the potatoes and placed into an extraction solution present in a container, such as a sealable tube, where the sprout inhibitor residue is extracted from the potato. In this manner, the amount of sprout inhibitor residue on the potato is captured at the time of sampling instead of when the entire potato arrives at the laboratory. Also, since only a representative sample of the potato is being transported to the laboratory instead of the entire potato, shipping costs are reduced. For instance, the potato sample that is transported to the laboratory will have a mass of about 5 grams of tissue present in a 30 ml vial as opposed to transporting 4-6 bulky potatoes which weigh about 1 kilogram. The savings in transportation costs may be significant when the potato samples are transported between states or from one continent to another. Shipping the representative sample in the smaller container eliminates the need for using specialized, bulk mailing services and packages. Instead, regular mail can be used to send the container (sealed tube) to the laboratory of choice. Further, since the sprout inhibitor residue is captured in an extraction solution that resists freezing, the shipped samples will resist freezing in the winter months, unlike the shipping of whole potatoes that may freeze during transport to the laboratory.

Referring now to FIG. 1, there is shown an exemplary embodiment of a kit used to collect a sample from the potato at a first location, such as a storage facility, generally at 10. The kit 10 may include gloves 12, such as disposable, latex gloves which are to be worn by a person handling and sampling the potatoes in order to prevent contamination of the sample and protect the person from exposure to any chemicals. The kit 10 may also include written instructions to instruct the person sampling the potatoes how to properly take the tissue samples from the potatoes and/or a sample logbook 14 for recording data pertaining to the sampled potatoes. A sampling means or metal pipe 16 is also present in the kit 10 for removing a tissue sample from the potato. In one particular embodiment, the sampling means 16 is a beveled, cylindrical pipe for collecting a tissue sample core from the potato. In other exemplary embodiments, the sampling means 16 may comprise a cork borer, a melon baller, a knife, or any other device which is able to remove the sample from the potato.

The kit 10 may further include a knife 18 for removing the circular, tissue sample core from the potato. In the exemplary embodiment, the knife 18 is a three-inch paring knife, but it will be apparent by those of ordinary skill in the art that any other device which performs functions the same as, or equivalent to, the knife 18 described herein may also be used. Sealable containers 20 are also included in the kit 10. The containers 20 include a cap 22 for sealing the containers 20. In one exemplary embodiment, the containers 20 are 30 ml amber, glass jars, but it will apparent by those of ordinary skill in the art that the containers 20 may be any other type of vial, jar or tube capable of being sealed as is known in the art. The kit 10 may also include tape to more efficiently seal the containers 20. In other exemplary embodiments, the containers 20 may comprise any type of inert material that does not react with the constituents placed in the container 20 or the chemical to be assayed, including, without limitation, polyethylene, polypropylene, polyethylene terephthalate copolymer, Teflon® brand polymer containing materials, fluorinated high-density polyethylene, polymethyl pentene, polyvinyl chloride, polysulfone, other known materials, or combinations thereof.

In the kit 10, the containers 20 each include a predetermined amount of an extraction solution 24. In the exemplary embodiment, the extraction solution 24 includes 10 ml of a solvent including 70% ethanol and 30% trimethylpentane, by volume, which is appropriate for dissolving the sprout inhibitor DMN. The extraction solution 24 may be prepared in a 1 L amber bottle by adding appropriate quantities of ethanol and trimethylpentane to the amber bottle and thorough mixing. It will be apparent by those of ordinary skill in the art that the extraction solution 24 may comprise any other solvent suitable for dissolving target chemicals, such as 1,4 DMN, diisopropyl naphthalene (DIPN), and/or CIPC, as are known in the art. Other solvents that may be used include, without limitation, ethyl acetate, tributyl phosphate, cyclohexane, dichloromethane(methyl chloride), dibutyl ether, acetonitrile, toluene, heptane, substituted aromatic solvents, halogenated alkyl alcohols, ethers, organic solvents or any combination thereof. In addition, the extraction solution 24 may also include any type of alcohol including, but not limited to, methanol, ethanol, propanol, isopropanol, tetrahydrofurfuryl alcohol, or combinations thereof. Where practical, the solvent used in the kit 10 should have a low toxicity such that a user of the kit 10 will not have any adverse affect from exposure to the solvent when using the kit 10.

The extraction solution 24 is divided evenly within the containers 20 as is known in the art. The extraction solution 24 further comprises 50 μl of an internal standard which may be added to the solvent using a 100 μl pipette, as is known in the art. The internal standard can be any chemical known in the art that has a substantially similar molecular weight, volatility and polarity as the chemical being tested (e.g., sprout inhibitor or pesticide), as well as the corresponding extracts of the tested chemical. For example, where 1,4 DMN is being tested, a different dimethylnaphthalene can be used as the internal standard. In a particular embodiment of the invention, the internal standard will have a retention time similar (but not identical) to 1,4 DMN. In other words, a retention time in a Gas Chromatograph analysis should be 0.5-4 minutes earlier or later than the retention time for 1,4 DMN. In one exemplary embodiment, where 1,4 DMN is being tested, 1,6 DMN could function as an internal standard since it has a retention time that is approximately 1 minute earlier than 1,4 DMN. In contrast, 2,3 DMN is not desirable for use as an internal standard for testing 1,4 DMN because it has a retention time that is only seconds earlier than 1,4 DMN. In another particular embodiment, 2-ethylnaphthalene can be used as the internal standard for 1,4 DMN.

In a particular embodiment, the internal standard has a concentration of 1 mg/ml of 2-ethylnaphthalene in reagent alcohol, such that 50 µg of 2-ethylnaphthalene is placed in each container. By placing a known amount of the internal standard in the containers 20 before the kit 10 is sent to the user at the potato storage facility, the quantitative measurement performed on the tissue samples can be calibrated as will be discussed in more detail herein.

In one aspect of the method of the present invention, one or more containers 20 are transported to a second location, such as a potato storage facility. As previously described herein, the kit 10 includes written instructions and/or a sample logbook 14 to instruct the person collecting the samples how to properly collect the samples at the first location, such as a potato storage facility. The sample logbook 14 may be used to record pertinent potato sample information, such as the location of the storage facility, the date the potato sample is collected, the type of potato sampled, the number of potatoes sampled, the location of where the sample is taken within the storage facility, the environmental conditions present in the storage facility, and any other pertinent information. The sample logbook 14 may also be transported to the second location. Alternatively, information contained in the logbook 14 can be communicated through other means, such as, for example, telephone, facsimile, or e-mail. To prevent any contaminants from distorting the sampling procedure, a user of the kit 10 should put on the gloves 12 before handling and sampling the potatoes.

The sampling procedure may be performed by collecting a tissue sample from one or more potatoes. In the exemplary embodiment, the potato samples are taken from a potato pile at the potato storage facility. Prior to collecting the tissue samples from the potatoes, the potatoes are lightly washed with water and rubbed to remove any dirt from the surface of the potato. During the light wash, care should be taken to ensure that any of the skin or russet netting of the potato is not removed from the surface of the potato. If the tissue samples are taken from a single potato, two peel samples (constituting the tissue samples) may be removed from each apical end (the end of the potato that has the highest concentration of buds) on opposing sides of the potato to produce a total of four tissue samples. If the tissue samples are taken from two separate potatoes, one peel sample may be removed from the basil end of the potato (the stem end of the potato where the tuber is attached to the plant) and one peel sample may be removed from the apical end on the opposing side of each of the two potatoes to produce a total of four tissue samples. If the tissue samples are taken from four separate potatoes, one peel sample may be removed from the center portion of each of the four potatoes to produce the four tissue samples.

In other exemplary embodiments, the step of washing the potato may be eliminated. For instance, since the chemical DMN is absorbed, at least partially, into the skin of the potato, the light washing will not remove the DMN adsorbed by the surface of the potato. However, other chemicals or sprout inhibitors (e.g., CIPC) may not be as efficiently absorbed by the potato, but instead may deposit on the surface of the potato. In these embodiments, the washing step may be omitted and the potato carefully sampled to ensure that no dirt is collected when the tissue sample is collected from the potato.

In a particular embodiment, the peel samples are removed from the potato by inserting a 2.1 cm diameter metal pipe 16 into the potato. For instance, if one potato is sampled, the metal pipe 16 is inserted into the potato four times in four different locations. The metal pipe 16 should be inserted into the potato to a depth of about 5 mm. The metal pipe 16 is removed from the potato and results in a circular cut, or a peel core sample, into the surface of the potato. In another exemplary embodiment, an outer surface of the metal pipe 16 may be marked with an indicia about 5 mm from an end of the metal pipe 16 that is to be inserted into the potato such that a user will know how far to insert the metal pipe 16 into the potato based on the indicia. If necessary, the knife 18 may be used to disconnect the circularly cut, peel core sample from the potato. The potato peel core sample, removed from the potato by this technique, should be about 1.3 mm to about 1.5 mm in length, resulting in a peel core sample about 2.1 cm in diameter and about 1.3 mm to about 1.5 mm in length. As previously discussed, the sampling means 16 and the size and shape of the extracted potato peel core are not limited to use of a metal pipe having a defined size and shape.

Each peel core removed from the potato is cut in half such that each peel core half may be easily deposited into the container 20 of the kit 10. The peel core can be cut in half after the peel core is disconnected, or removed, from the potato, but while the peel core in still in the position of the circular cut in the potato. Each half of the peel core is placed into the container 20 using the knife 18 to minimize any contamination. In another exemplary embodiment, the peel cores may be removed from the potatoes, collected in a receptacle, such as a disposable, plastic weigh boat, and cut in half in the receptacle before being placed in the container 20. No matter what method is used to collect the peel cores from the potatoes, care should be taken such that the core halves are not touched by the hands of the user or any other possible source of contamination. In another exemplary embodiment, four peel cores from the potatoes are removed such that each core has a length of about 5 mm and is cut into four strips instead of halves, each strip being about 5 mm wide. The strips of the four peel cores, whether cut in half or in four strips, should be deposited into one container 20 including the extraction solution 24. By placing all four cores from the potatoes in the same container 20, accurate quantitative measurement can be made at the second location.

In the exemplary embodiment, the containers 20 are configured such that they may be labeled with an identification number, a potato storage name, a collection date, and/or the name of the sample taker to track or identify the potato samples. For instance, the containers 20 may have a blank area on the outside of the container 20 that is configured to receive ink from a pen. Alternatively, adhesive labels may be provided, wherein the adhesive labels may have information printed thereon and adhered to the outside of the containers 20. Once the potato samples have been collected from the potato storage facility, the containers 20 should be sealed with the caps 22 and optionally taped such that the containers 20 including the potato samples will not leak during transport. The potato samples are then ready to be transported, or shipped via ground or air, to the second location, such as a laboratory, wherein the amount of sprout inhibitor residue on the potato samples may be assayed.

The kits 10 of the present invention may include any number of containers 20 and may be configured to securely hold the containers 20 during shipping. As known in the art, the kits 10 may comprise a box-type structure that is configured, such as with packaging material, to securely hold the various components of the kit 10 as described herein. Further, the kits 10 may be configured to be reused such that, once the kits 10 (including unused containers 20) arrive at the potato storage facility, the containers 20 may have tissue samples placed therein and the filled containers 20 are placed back into the kit 10 for transport. The kit 10 including the containers 20 and the tissue samples may also be configured with shipping labels for the convenience of the user such that the kits 10 may be conveniently shipped to the second location, or the laboratory, for testing. Alternatively, the shipping labels may be configured for attachment to the filled containers 20, so that the filled containers 20 can be shipped to the second location.

Another aspect of the invention relates to a system, including the kit 10, used to perform the methods of the present invention. The system includes a source of a sample, such as a pile of potatoes where the potato tissue samples are collected, the kit 10, and a laboratory or testing facility. Once the samples are collected and arrive at the laboratory, the containers 20 including the potato tissue samples are removed from the kit 10 and are shaken for a sufficient period of time (e.g., 10 seconds). The containers 20 are placed into a water bath that is set at a predetermined temperature, such as from about 45° C. to about 55° C. The containers 20 are allowed to set in the water bath for a sufficient time to allow the same to be warmed (e.g., about 15 minutes). In the exemplary embodiment, the water bath used to heat the containers 20 is heated with a hot plate, such as those available from Toastmaster Eclipse, to the temperature of about 45° C. to about 55° C. After heating, the containers 20 are again shaken for about 5 seconds.

After the containers 20 are removed from the water bath, the liquid including the extraction solution 24 is transferred to a separate container (such as a 10 ml flat bottom Erlenmeyer flask) using a funnel (e.g., a 4 cm funnel) and a pipette (e.g., a 9 inch disposable pipette). The solid peel sample is left in the container 20. A suitable solvent, such as 1 ml of a 0.2 M NaCl solution, is added to the extraction solution 24 in the Erlenmeyer flask to aid in the separation of an aqueous and/or alcohol layer from an organic layer in the extraction solution 24. The extraction solution 24 is allowed to cool, during which time the suspended precipitates in the extraction solution 24 fall out of solution and are deposited on the bottom of the Erlenmeyer flask.

After the extraction solution 24 has been allowed to set and cool, the extraction solution separates into the aqueous and/or alcohol layer (top layer) and the organic layer (bottom layer). 2 ml of liquid, including the solvent (e.g., trimethylpentane), in the aqueous (top) layer is removed from the extraction solution 24 and placed into an auto-sampler vial. The auto-sampler vial is sealed with a solid cap and the contents of the auto-sampler vial may be analyzed using gas chromatography in a separation device that separates the chemicals present in the extraction solution 24. Suitable auto-sampler vials can be made of any suitable material and can be of any suitable shape and size. In one particular embodiment, the auto-sampler vial can have a capacity of 2 mls. In the exemplary embodiment, the separation device can be a High Performance Liquid Chromatograph (HPLC), or any other types of gas chromatograph, as are known in the art. In other exemplary embodiments, the separation device may comprise any other type of separation device that uses other known techniques for separating chemicals including, but not limited to, gel electrophoresis. In the exemplary embodiment, the separation device is used to quantitatively measure the amount of sprout inhibitor (e.g., DMN and or CIPC), present in the auto-sampler vial, wherein the amount of sprout inhibitor in the auto-sampler vial is converted or extrapolated to calculate or estimate the amount of sprout inhibitor on the potato that was removed from the potato pile at the potato storage facility.

The amount of internal standard in the extraction solution is also quantified with the separation device. If the quantitated amount of the internal standard (Q) does not substantially equal the known amount of internal standard (K) placed in the containers, then the quantitated amount of sprout inhibitor may be calibrated using a ratio (R). For the calibration, it will be assumed that no internal standard is lost from the container from the time the internal standard is placed in the container until the sample is collected and placed into the container. To calculate the ratio, the quantitated amount of the internal standard (Q) is compared to the known amount of the internal standard (K). For example, if the amount of quantified internal standard is 40 μg (Q=40) and the known amount of internal standard is 50 μg (K=50), the ratio (R) is determined by dividing the quantitated amount of internal standard (Q) by the known amount of the internal standard (K): Q/K=R. In the exemplary embodiment, the calculation is 40/50=0.8. The calculated ratio may be used to calibrate the amount of sprout inhibitor by multiplying the measured amount of sprout inhibitor by the ratio (R). The calibration assumes that the internal standard is equally volatile to the type of sprout inhibitor. Where volatility between the internal standard and the tested chemicals differs, a volatility ratio may also be incorporated into the calculations by taking into account the volatility differential between the internal standard and the tested chemical.

In another exemplary embodiment, the comparison of the quantitated amount of the internal standard (Q) to the known amount of the internal standard (K) may be used as a qualitative check to help ensure the accuracy of the test. For instance, instead of calculating the ratio (R), the comparison may be used to discard measurement results of samples where the quantitated amount of the internal standard (Q) does not substantially equate to the known amount of internal standard (K) placed in the containers. In this exemplary embodiment, any data obtained from samples where K and Q are not substantially the same is discarded and the sample may be recollected.

To demonstrate that the methods and kit of the present invention quantitatively measure the sprout inhibitor in a manner similar to that of conventional testing methods, duplicate tissue samples were taken from potatoes in the laboratory on a single day. A group of tissue samples designated as Group I were cut from the potatoes and the amount of sprout suppressant was quantitatively measured on the same day that the tissue samples were cut from the potatoes. A group of tissue samples designated as Group II were cut from the potatoes on the same day as Group I, but the amount of sprout suppressant in the tissue samples of Group II was not quantitatively measured until 1 week after collection, wherein the tissue samples were stored in containers 20 and extraction solution 24, as described with reference to FIG. 1. Thus, the tissue samples of Group II were simulated to have been collected at another location (i.e., potato storage facility) and shipped to the laboratory for testing. The amount of sprout suppressant present and quantitatively measured in the tissue samples of Groups I and II are presented in Table I.

The quantitated amount of sprout inhibitor present on the surface of the potato was calculated in the following manner. Four cores were collected from the potato, each having a core size of about 2.1 cm in diameter, wherein the collective surface area of the four cores was about 10% of the total surface area of a potato having a mass of approximately 250 g. Alternatively, it is understood that each of the four cores can be collected from individual potatoes. To calculate the amount of sprout suppressant (1,4 DMN) on the potato surface, the amount of DMN in the extraction solution quantitated by the separation device was multiplied by 10 (to arrive at 100%) and divided by 250 (since the potato was assumed to have a mass of about 250 g) to arrive at ppm per gram of potato. If the calibrated ratio (R) is used based on the measurement of the internal standard, the amount of sprout suppressant quantitated from the extraction solution should be multiplied by the calculated ratio (R).

TABLE I

| Potato | Group I 1,4 DMN Concentration | Group II 1,4 DMN Concentration |
|---|---|---|
| A | 0.88 ppm | 0.93 ppm |
| B | 0.91 ppm | 0.91 ppm |
| C | 0.29 ppm | 0.31 ppm |
| D | 0.61 ppm | 0.74 ppm |
| E | 0.66 ppm | 0.69 ppm |

As is demonstrated by the data of Table I, the amount of sprout inhibitor quantitated from Group I and Group II is substantially the same, where there is an average increase of about 7% from Group I to Group II. The slight increase in sprout inhibitor concentration may be due to the longer extraction time (i.e., one week in the containers) that the tissue samples of Group II were present in the extraction solution. An alternative formula that can be used to calculate the amount of sprout suppressant (e.g., DMN) includes:

[Peak Area of 1,4DMN]/[Peak Area of 2EN]×[response factor]×[amount of 2EN added to bottle (ug)]×10/250

The response factor is obtained from the calibration curve plotting the ration of PA 1,4DMN/PA 2EN (on y-axes) against amount of 1,4DMN/amount of 2EN in the calibration solutions.

In another model test system, groups of tissue samples collected from potatoes were designated as Groups III and IV, wherein the tissue samples of Group III were collected from potatoes on the same day that the amount of sprout inhibitor on the potato sample was quantitatively measured. In Group IV, the tissue samples were collected on the same day as the tissue samples of Group III, but the tissue samples were stored in the extraction solution in the containers 20 for six days. Results of the determination of sprout inhibitor concentration are presented in Table II.

TABLE II

| Potato | Group III 1,4 DMN Concentration | Group IV 1,4 DMN Concentration |
|---|---|---|
| F | 0.24 ppm | 0.25 ppm |
| G | 0.19 ppm | 0.19 ppm |

The results in Table II are substantially the same as the results of Table I indicating that the containers 20 of the kit 10 and the methods of the present invention allow for the successful collection of tissue samples from tubers at a first location, such as a potato storage facility, and subsequent quantitative measurement of an amount of the sprout inhibitor on the tissue culture samples of the tubers at a second location, such as a laboratory.

In another model test system, groups of tissue samples collected from potatoes were designated as Groups V and VI, wherein the tissue samples of Group V were collected from potatoes on the same day that the amount of sprout inhibitor on the potato sample was quantitatively measured. In Group VI, the tissue samples were collected on the same day as the tissue samples of Group V, but the tissue samples were stored in extraction solvent in the containers for seven days. Results of the determination of sprout inhibitor concentration are presented in Table III.

TABLE III

| Potato | Group V 1,4 DMN Concentration | Group VI 1,4 DMN Concentration |
|---|---|---|
| H | 0.69 ppm | 0.73 ppm |
| I | 0.30 ppm | 0.31 ppm |

The results in Table III are substantially the same as the results from Tables I and II further indicating the efficacy of the methods, kit and system of the present invention.

The embodiments described herein are not meant to limit the scope of the present invention. In each of the various embodiments, the methods, kits and system described herein disclose a way for collecting a sample and transporting the sample to another location for chemical residue analysis. However, the present invention may be carried out using embodiments different from those specifically described herein. Therefore, the scope of the present invention is not limited by the exemplary embodiments, but is defined by the appended claims.

What is claimed is:

1. A kit for transporting a tuber sample from a crop storage facility to a chemical analysis facility, the kit comprising:
   a container configured to hold and transport the tuber sample from the crop storage facility to the chemical analysis facility, wherein the container comprises an extraction solution for dissolving a sprout inhibitor in the tuber sample, the sprout inhibitor having a volatility that is substantially the same as ethylnaphthalene; and
   ethylnaphthalene for calibrating a quantitative measurement of the sprout inhibitor.

2. A kit for transporting a tuber sample comprising a sprout inhibitor from a crop storage facility to a chemical analysis facility, the kit comprising:
   a logbook for recording information about the tuber sample;
   instructions for how to use the kit; and
   a container configured to hold and transport the tuber sample, wherein the container comprises:
      a sampling means for collecting the tuber sample from a tuber;
      an extraction solution comprising ethanol and trimethylpentane, for dissolving the sprout inhibitor comprised within the tuber sample, wherein the sprout inhibitor is a substituted naphthalene or chlorpropham;
      an internal standard comprising ethylnaphthalene for calibrating a quantitative measurement of the sprout inhibitor at the chemical analysis facility; and
      a label identifying a known amount of the internal standard.

* * * * *